US009011384B2

(12) United States Patent
Heddon

(10) Patent No.: US 9,011,384 B2
(45) Date of Patent: Apr. 21, 2015

(54) OUTER EAR BONE ANCHOR

(76) Inventor: Chris Heddon, Evanston, IL (US)

(*) Notice: Subject to any disclaimer, the term of this patent is extended or adjusted under 35 U.S.C. 154(b) by 549 days.

(21) Appl. No.: 13/414,701

(22) Filed: Mar. 7, 2012

(65) Prior Publication Data

US 2012/0330278 A1 Dec. 27, 2012

Related U.S. Application Data

(60) Provisional application No. 61/449,800, filed on Mar. 7, 2011.

(51) Int. Cl.
A61M 25/02 (2006.01)
H04R 25/00 (2006.01)
A61M 25/04 (2006.01)
A61F 2/18 (2006.01)

(52) U.S. Cl.
CPC .............. *H04R 25/606* (2013.01); *A61M 25/04* (2013.01); *A61F 2002/183* (2013.01)

(58) Field of Classification Search
USPC ......... 604/27, 43, 48, 73, 104, 106–109, 174, 604/175, 509, 514
See application file for complete search history.

(56) References Cited

U.S. PATENT DOCUMENTS

| 6,377,849 | B1 | 4/2002 | Lenarz et al. |
| 6,648,873 | B2 | 11/2003 | Arenberg et al. |
| 2003/0097121 | A1 | 5/2003 | Jolly et al. |
| 2009/0012594 | A1 | 1/2009 | Gibson |
| 2009/0110223 | A1 | 4/2009 | Semcken |
| 2010/0137988 | A1 | 6/2010 | Markworth et al. |
| 2011/0160699 | A1* | 6/2011 | Imran ........................... 604/514 |
| 2011/0208161 | A1* | 8/2011 | Ivri ............................... 604/514 |

* cited by examiner

Primary Examiner — Theodore Stigell
Assistant Examiner — Amber Stiles
(74) Attorney, Agent, or Firm — Richards Patent Law P.C.

(57) ABSTRACT

An outer ear bone anchor to be stabilized within a person's external auditory canal includes: a body; and a plurality of anchor pins, each of the anchor pins including a first end and a second end such that, when the first end of each of the anchor pins is secured to the external auditory canal, the second end of each of the plurality of anchor pins stabilize the body within the external auditory canal. A method of delivering medication to a person's middle ear or inner ear, the method comprising the steps of: securing an outer ear bone anchor in the person's external auditory canal; securing an inner catheter to the outer ear bone anchor, the inner catheter extending to the person's middle ear or inner ear; and passing medication through inner catheter to the person's middle ear or inner ear.

7 Claims, 3 Drawing Sheets

OUTER EAR BONE ANCHOR

CROSS-REFERENCE TO RELATED APPLICATIONS

This application claims the benefit of U.S. Provisional Application No. 61/449,800, filed on Mar. 7, 2011, the entirety of which is incorporated herein by reference.

BACKGROUND OF THE INVENTION

The present subject matter relates generally to an outer ear bone anchor. More specifically, the present invention is a bone anchor that may be secured within the outer ear to provide a stable base to which other devices may attach, be stabilized or pass through.

The entirety of the disclosure of the following additional references is hereby incorporated into this disclosure: (1) Plontke S K, Zimmermann R, Zenner H, and Lowenheim. Technical note on microcather implantation for local inner ear drug delivery: surgical technique and safety aspects. Otology and Neurotology. 2006; 27: 912-917. (2) Silverstein H, Thompson J, Rosenburg S I, Brown N, and Light J. Silverstein MicroWick. Otolaryngology Clinics of North America. 2004; 37: 1019-1034, and (3) Thomsen J, Charabi S, and Tos, Mirko. Preliminary results of a new delivery system for gentamicin to the inner ear in patients with Meniere's disease. European Archives of Otolaryngology. 2000; 257: 362-365.

The ear divides anatomically into three sections: external auditory canal (EAC), the middle ear and the inner ear. The EAC consists of the auditory meatus (the opening of the ear), the canal itself, followed by the tympanic membrane (TM), which is the boundary between the EAC and the middle ear. The middle ear is an air-filled cavity within the temporal bone that contains the ear bones, which, from lateral to medial, are the malleus, incus, and stapes. The lateral wall of the middle ear is partially bound by the TM and the medial wall is bounded by the inner ear, which is encased in bone. The inner ear is comprised of the cochlea, which contains cells that detect sound, and the vestibular apparatus, which contains cells that detect motion. Both the cochlea and the vestibular apparatus are a maze of fluid-filled tubes that run through the temporal bone of the skull.

There are situations in which delivery of medication to the inner or middle ear may be advantageous. For example, there may be conditions, such as some forms of hearing loss, that may be positively affected by the use of medication as described in Melki, S. J., Heddon, C. M., Frankel, J. K., Levitt, A. H., Momin, S. R., Alagramam, K. N. and Megerian, C. A. (2010), Pharmacological protection of hearing loss in the mouse model of endolymphatic hydrops, The Laryngoscope, 120: 1637-1645. doi: 10.1002/lary.21018, the entirety of which is incorporated herein by reference. However, current delivery methods are invasive, and, in some instances, may harm the middle and/or inner ear.

Traditional invasive medication delivery methods, as detailed by Thomsen et al. 2000 and Plontke et al. 2006, include implanting a medication delivery pump and catheter under the skin and within the temporal bone of the patient, so that the delicate middle and inner ear structures are not harmed by transmission of external forces through the device that are the result of normal daily activity. This often requires extensive and intricate drilling of the temporal bone, which can result in damage to delicate cochlear and vestibular structures, middle ear structures, the brain, vascular structures and the facial nerve. This procedure also requires general anesthesia and hospital admission, both of which are significant sources of morbidity and mortality. The Silverstein MicroWick (Silverstein et al. 2004) is an alternate method for delivery of medication to the inner ear that involves using a polyacetate wick as a conduit for medications to be delivered to the inner ear via the round window membrane (RWM). The wick itself travels though TM via a pressure equalization tube (PE tube). Placement of this device is temporary and, after placement, the PE tube is meant to be used intermittently in the treatment of sudden sensorineural hearing loss, vertiginous symptoms of Meniere's disease, and diseases that do not necessarily require continuous drug infusion. Aside from the temporary nature of PE tube placement, the wick must be replaced every four weeks in order to prevent adhesion to middle ear mucosa. These and other current methods of medication delivery to the middle and inner ear are invasive, painful, and in some instances, ineffective.

There are disease states of the cochlea and vestibular system that would benefit greatly from continuous infusion of therapeutic agent (including, but not limited to medications, growth factors, nanoparticles, genetic factors), as continuous delivery optimally treats the most distal portions of the cochlea and vestibular structures. The superiority of continuous drug delivery over intermittent delivery in treating the entire hearing and vestibular apparatus has been shown in computer, animal and human models.

In addition to medication delivery, there are other conditions and procedures that involve the placement of materials into the middle or inner ear. In one such example, hearing aids utilizing cochlear implants require the implantation of an electrode array in the inner ear, the electrode is then connected to an associated receiver. In order to prevent damage to the sensitive portions of the middle and inner ear, cochlear implants have been implanted by drilling through the mastoid bone, located behind the ear, rather than being implanted through the ear itself. There are other implantable hearing devices that require drilling into the temporal bone. Use of these devices could be augmented or supplanted by the incorporation of an outer ear bone anchor, as provided herein. The devices that would benefit most include, but are not limited to, bone anchored hearing aids (BAHAs) and middle ear implants. In some iterations, an external receiver resting behind the inner ear could be easily connected and disconnected to/from a wire that sits at the external auditory meatus and more distally attaches to the bone anchor. The configuration from the point of the anchor inward would depend upon the nature of the device. For a BAHA or middle ear implant type device, a vibrating element may emanate from the hardware attached to the anchor and may contact the ossicles, the medial wall of the middle ear, the round window, the oval window or some other portion of the ear. The mechanism of the vibrating element could be piezoelectric, magnetic or electromagnetic. In other iterations, the receiver could be miniaturized and placed entirely within the middle ear with the canal-based anchor serving as the anchor point for the entire device.

As shown, there are numerous situations in which access to the middle and inner ear involves invasive drilling through the bone structure surrounding the ear or other invasive or potentially damaging action. Accordingly, there is a need for device and method adapted to provide access to the inner and middle ear that is less invasive and has a lower potential for harm to the patient.

BRIEF SUMMARY OF THE INVENTION

In order to meet the existing need to provide access to the inner and middle ear in a less invasive and less potentially harmful manner, the present subject matter discloses an outer ear bone anchor that may be secured within the EAC to provide a stable base to which other devices may attach, be stabilized or pass through. In a preferred embodiment, the outer ear bone anchor is a small structure that may be inserted into and secured within the inner ⅔ of the EAC and in close proximity to the TM. In some embodiments, the outer ear bone anchor includes a passage through the body of the anchor to which tubes may be connected at both sides. For purposes of the subject matter disclosed herein, the side of the bone anchor that faces towards the outside of the ear will be referred to as the front face, and the side of the bone anchor that faces towards the inside of the ear will be referred to as the rear face.

The bone anchor may be mounted to the bony portion of the EAC by one or more deployable anchor pins. When placed in the EAC in the position desired for implantation, a deployment mechanism may be activated such that the anchor pins deploy to stabilize the bone anchor in the EAC.

In some embodiments of the bone anchor, front and rear connectors allow catheter tubes (or similar devices) to attach to the front and rear faces of the bone anchor. In such embodiments, the front connector may be located at the opening of the passage on the front face, and the rear connector may be located at the opening of the passage on the rear face. The front and rear connectors enable catheter tubes to attach to either side of the bone anchor. When tubes are connected to the bone anchor, a continuous fluid-tight connection may be made from an outer pump, through the tubes, to the inner ear.

In other embodiments, the bone anchor may not include one or more passages. For example, the outer ear bone anchor may be used to provide a stable base onto which devices may be secured in close proximity to the eardrum or other middle and inner ear structures. In still further embodiments, the bone anchor may be used to stabilize other materials or devices that may be implanted into or passed through the inner and middle ears.

An example of an outer ear bone anchor to be stabilized within a person's external auditory canal includes: a body; and a plurality of anchor pins, each of the anchor pins including a first end and a second end such that, when the first end of each of the anchor pins is secured to the external auditory canal, the second end of each of the plurality of anchor pins stabilize the body within the external auditory canal. The plurality of anchor pins may form a portion of an anchoring mechanism. The anchoring mechanism may include a deployment mechanism adapted to move the anchor pins from a pre-deployed position to a deployed position. The deployment mechanism may include a gear with a first set of teeth adapted to engage one or more of the plurality of anchor pins and a second set of teeth to engage a deployment tool. The plurality of anchor pins may include teeth to engage the first set of teeth of the gear. The plurality of anchor pins mate with one common gear or there may be more than one gear that mates with a subset of the plurality of anchor pins. The body may form a passage from a front face of the body to a rear face of the body. The body may further include a front connector located adjacent to an opening of the passage at the front face and a rear connector located adjacent to an opening of the passage at the rear face. The body may further include an outer catheter secured to the front connector and an inner catheter secured to the rear connector forming a fluid-tight passage from the outer catheter to the inner catheter.

A method of delivering medication to a person's middle ear or inner ear may include the steps of: securing an outer ear bone anchor in the person's external auditory canal; securing an inner catheter to the outer ear bone anchor, the inner catheter extending to the person's middle ear or inner ear; and passing medication through inner catheter to the person's middle ear or inner ear. The method may further include the step of securing an outer catheter to the outer ear bone anchor wherein the inner catheter and the outer catheter are connected to form a fluid-tight passage through the outer ear bone anchor. The method may further include the step of connecting the outer catheter to a pump to deliver a continuous flow of medication over a duration of time. The outer ear bone anchor used in the method may include: a body; and a plurality of anchor pins, each of the anchor pins including a first end and a second end such that, when the first end of each of the anchor pins is secured to the external auditory canal, the second end of each of the plurality of anchor pins stabilize the body within the external auditory canal.

Another example of an outer ear bone anchor to be stabilized within a person's external auditory canal includes: a body including a front face, a rear face, and a passage formed through the body extending from the front face to the rear face, the body further including a front face connector located adjacent to an opening of the passage at the front face and a rear face connector located adjacent to an opening of the passage at the rear face; and an anchoring mechanism including a deployment mechanism and a plurality of anchor pins, wherein the deployment mechanism includes a gear with a first set of teeth adapted to engage one or more of the plurality of anchor pins and a second set of teeth to engage a deployment tool, wherein the plurality of anchor pins include teeth to engage the first set of teeth of the gear, further wherein each of the anchor pins includes a first end and a second end such that, when the first end of each of the anchor pins is secured to the external auditory canal, the second end of each of the plurality of anchor pins stabilizes the body within the external auditory canal.

An advantage of the bone anchor is that enables a catheter to deliver medication to the middle or inner ear without tunneling through any bone or under or through any skin (excluding the TM).

Another advantage of the bone anchor is that it is minimally invasive.

Another advantage of the bone anchor is that it provides a stable base allowing other devices to be connected.

A further advantage of the bone anchor is that it is not traumatic or damaging to inner ear structures.

Yet another advantage of the bone anchor is that it can be used by patients with a high activity level without the danger of transmission of external forces to delicate inner and middle ear structures.

Another advantage of the bone anchor is that it is aesthetically pleasing and comfortable for the user.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements

DETAILED DESCRIPTION OF THE INVENTION

Figure 1:
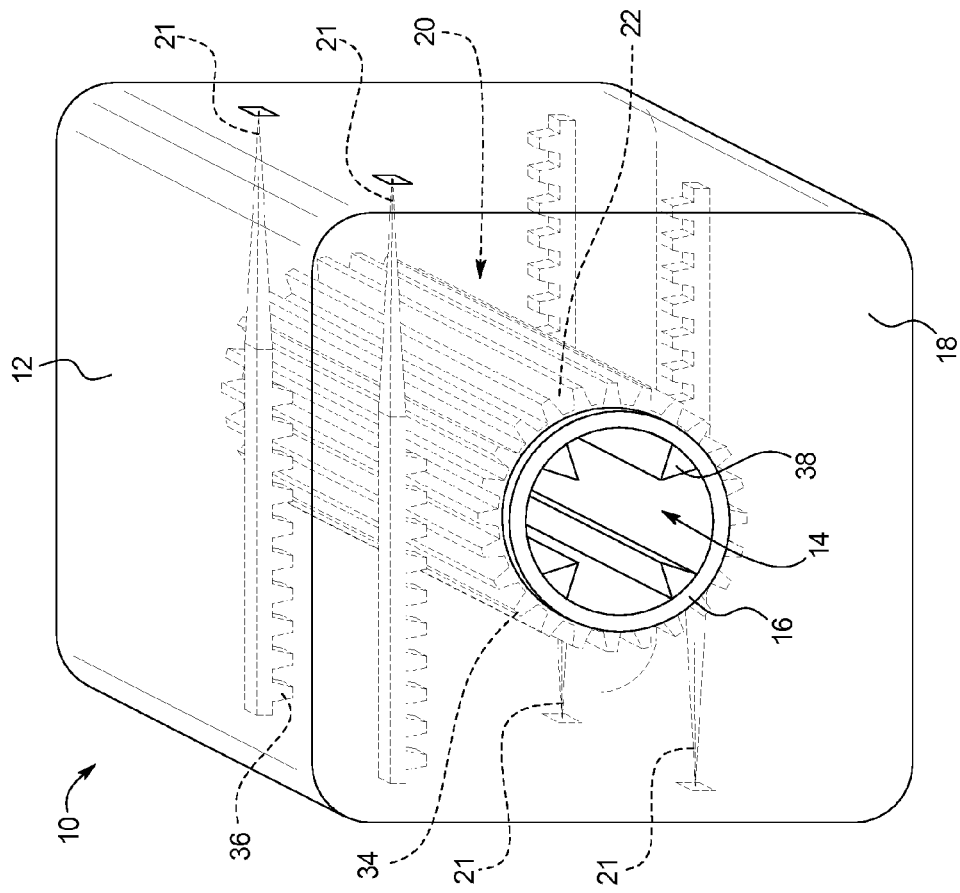
FIG. 1 is a front perspective view of an outer ear bone anchor.

FIG. 1 illustrates an example of an outer ear bone anchor 10. As shown in FIG. 1, the bone anchor 10 includes a body 12 and a passage 14. The body 12 shown in FIG. 1 is formed from a structural polymer. However, it is contemplated that the bone anchor 10 may be formed from any structural material suited for placement within the external auditory canal (EAC). Since the bone anchor 10 is intended to be placed inside the EAC, the bone anchor 10 may be formed with materials that can be easily cleaned and sterilized, if needed.

In the example shown in FIG. 1, the bone anchor 10 is generally shaped as a cube. However, it is contemplated that the bone anchor 10 may be cylindrical, cuboid, or any other shape suitable for implantation within the EAC.

As shown in FIG. 1, the bone anchor 10 includes a central passage 14 extending from the front face 18 of the bone anchor 10 to the rear face 24 of the bone anchor 10. In the example shown in FIG. 1, the passage 14 is used to connect an outer catheter 28 to an inner catheter 30, as will be described further herein. In other embodiments, it is contemplated that the passage 14 may be used to stabilize one or more devices in the outer ear or passing through into the middle and/or inner ears. In still further embodiments, the bone anchor 10 may not include a passage 14 or may include multiple passages 14. For example, in one contemplated embodiment, the bone anchor 10 does not include a passage 14, but further includes a mounting portion to which one or more devices may be mounted or otherwise secured.

Figure 3:
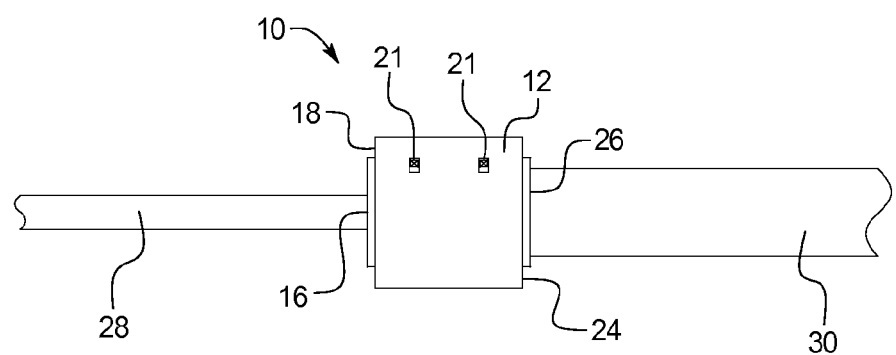
FIG. 3 is a side view of the bone anchor wherein inner and outer catheters are attached to show the continuous fluid tight connection from the outer to inner sides of the bone anchor.
Figure 4:
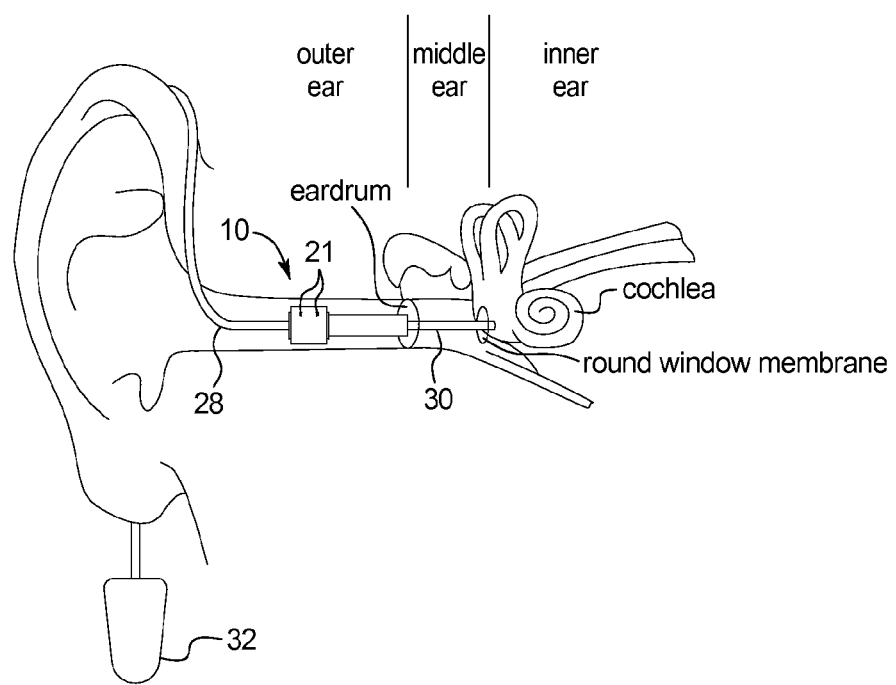
FIG. 4 is a view of the bone anchor in place in the ear canal connected to a pump and extending into the target zone of the ear.

In the example shown in FIG. 1, a front connector 16 is provided on the front face 18 of the bone anchor 10 for mating with an outer catheter 28 (shown in FIGS. 3 and 4). The front connector 16 enables the outer catheter 28 to attach to the passage 14 with a fluid tight seal. Similarly, as shown in FIG. 3, a rear connector 26 is provided on the rear face 24 of the bone anchor 10 for mating with an inner catheter 30 (shown in FIGS. 3 and 4), enabling the inner catheter 30 to attach to the passage 14 with a fluid tight seal. As will be recognized by one skilled in the art based on the disclosures provided herein, the front connector 16 and rear connector 26 may vary in size, shape, and other configuration to appropriately mate with the objects to be secured thereto.

As further shown in FIG. 1, the embodiment of the bone anchor 10 depicted includes an anchor mechanism 20. In the example shown in FIG. 1, the anchor mechanism 20 includes a plurality of anchor pins 21 and a deployment mechanism 22. In the example shown in FIG. 1, there are four anchor pins 21 provided such that they may be deployed through opposing sides of the bone anchor 10. However, it is contemplated that there may be a greater or lesser number of deployment pins 21, that the one or more anchor pins 21 may alternatively be positioned on the bone anchor 10 (e.g., extend from three sides of a triangular cylindrical body 12), that the anchor pins 21 may extend at any angle relative to the body 12.

The anchor pins 21 shown in FIG. 1 are adapted to secure the bone anchor 10 into the bone structure surrounding the EAC. Accordingly, the anchor pins 21 are made from a material appropriate for penetrating the EAC and anchoring into the underlying bone structure. The anchor pins 21 shown in FIG. 1 are formed from materials that will integrate into the bone of the EAC. Titanium coated with hydroxyapatite is one example of a material appropriate to serve this purpose. In this example, titanium is selected for its excellent biocompatibility, because it is MRI compatible, electrocautery compatible and easily moldable. Alternatively, amorphous metal alloys, like Liquidmetal, may be used as they are moldable like plastic to nanometer scale and can be formulated to integrate with bone. It is contemplated that materials with lower coefficients of restitution may create lower harmonic distortion in cases where the anchor is used as part of a hearing device that relies on vibration. However, it is contemplated that the anchor pins 21 may be formed from any material capable of securing the bone anchor 10 into the bone structure surrounding the EAC.

As further shown in FIG. 1, the anchor mechanisms 20 may include one or more deployment mechanisms 22 for deploying the anchor pins 21 at a desired time. In the example shown in FIG. 1, the deployment mechanism 22 is an axially rotating, externally and internally toothed, gear. The external teeth 34 of the deployment mechanism 22 mate with corresponding teeth 36 along the length of the anchor pins 21 such that rotation of the deployment mechanism 22 drives the anchor pins 21 into or out of the body 12 of the bone anchor 10. The internal teeth 38 of the deployment mechanism 22 mate with a driving tool (not shown) such that a user may activate the deployment mechanism 22 after the bone anchor 10 has been placed within the EAC. Accordingly, the bone anchor 10 may be placed within the ear canal before the anchor pins 21 are deployed to secure the bone anchor 10 in place.

The anchor mechanism 20 shown in FIG. 1 is merely one example of an anchor mechanism 20 that may be appropriate for the bone anchor 10. In one contemplated embodiment, the anchor mechanism 20 may include a series of spring-loaded anchor pins 21 deployable by activating a release mechanism to enable the anchor pins 21 to be driven outward from the body 12. In another contemplated embodiment, screws may be used as a part of the anchor mechanisms 20, though it is understood that it may be awkward to drive the screws considering their placement. In another example, the anchor mechanism 20 may be an independent, separable, portion of the bone anchor 10 that includes anchor pins 21 that may be driven simultaneously from a "disengaged" position to an "engaged" position. In such case, the anchor mechanism 20 is positioned within the EAC with the anchor pins 21 in the disengaged position. Then, when properly positioned, the anchor pins 21 are driven to the engaged position to secure the anchor mechanism 20 in place within the EAC. Then, the remaining structure of the bone anchor 10 may be attached to the secured attachment mechanisms 20. For example, the separable portions of the bone anchor 10 may be snapped together or may have other mating and/or locking portions to secure the elements together. In using the embodiment shown in FIG. 1 as an example, the body 12 may be the separable portion of the bone anchor 10 that is mated onto the anchor mechanism 20 after the anchor pins 21 have been deployed to secure the anchor mechanism 20 in place within the EAC.

In yet other contemplated examples of the bone anchor 10, a plurality of anchor pins 21 may be first set independently and then the remaining elements of the bone anchor 10 may be built onto (i.e., connected onto) the placed anchor pins 21. For example, the body 12 may be provided in multiple pieces. In such an example, a rear portion of the body 12 may be attached to the anchor pins 21 after the anchor pins 21 are placed. First, any rearward facing elements of the bone anchor 10 (i.e., rear catheter, etc.) may be connected to the rear portion of the body 12; the rear portion of the body is connected to the anchor pins 21. Then, the front portion of the body 12 may be attached to the rear portion, along with any front facing elements of the bone anchor 10. The various portions of the bone anchor 10 may be provided with any beneficial alignment, connection and/or other guides or mechanisms to ensure proper placement and secure engagement. In such an example, the anchor mechanism 20 may include only a plurality of anchor pins 21 and not a specific deployment mechanism 22.

If present, the deployment mechanisms 22 may or may not require a special tool for ensuring the appropriate deployment depth and/or force is applied. For example, an appropriately adapted torque screwdriver may be used to control the deployment depth of and/or force applied to the anchor pins 21. Accordingly, it is considered that a specialized deployment tool may be used to place and secure the bone anchor 10.

In one example, the deployment tool may be configured to hold the attachment mechanism 20 at the tool's distal end. At the tool's proximal end, a control may be provided to control the deployment of the anchor mechanism 20. The control may include or be associated with a depth and/or torque reading to ensure proper placement and engagement of the anchor mechanism 20. The control itself may be a torque-limited control such as a torque-limited knob that deploys the anchor pins 21 (or other elements of the anchor mechanism 20) at a predetermined depth and/or force. The tool may further include an integrated wide-angle fiber optic camera/scope to assist with placement as the tool itself may partially obstruct the user's view to the placement target.

Figure 2:
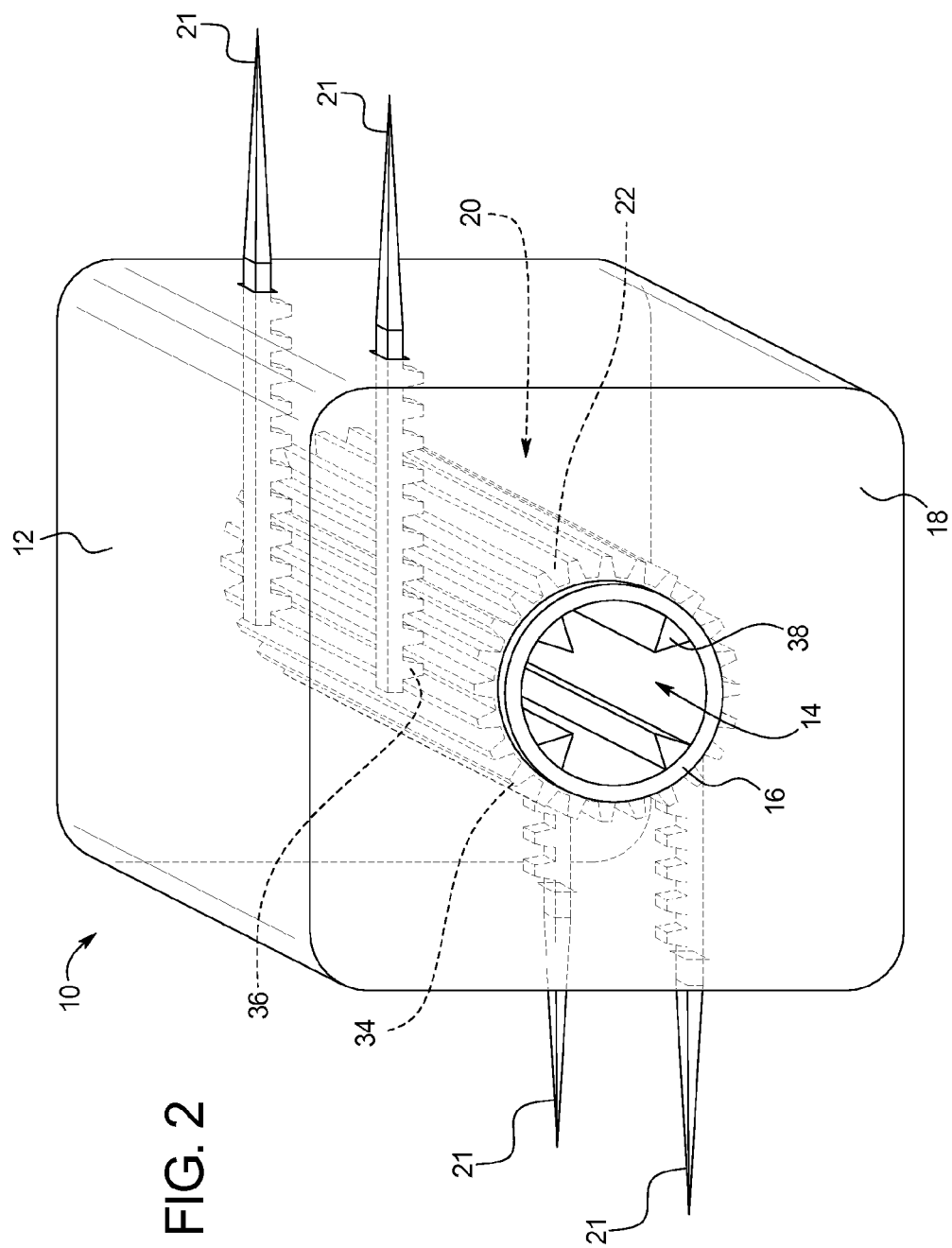
FIG. 2 is a front perspective view of the bone anchor shown in FIG. 1 with the anchor mechanisms deployed.

In the example of the bone anchor 10 shown in FIG. 1, the anchor pins 21 are shown in a retracted or "pre-deployment" position. Turning now to FIG. 2, the anchor pins 21 are shown in an extended or "deployed" position resulting from the activation of the deployment mechanism 22 (e.g., the turning of the gear). The deployment of the anchor pins 21 may cause the anchor pins 21 to penetrate the bony portion of EAC to secure the bone anchor 10 in place within the ear canal. In the example shown in FIGS. 1 and 2, once the bone anchor 10 is in position and the deployment mechanism 22 has been activated, the outer catheter 28 and the inner catheter 30 may be attached to the bone anchor 10 as shown in FIG. 3.

Turning now to FIG. 3, the illustrated example shows the outer catheter 28 connected to the front connector 16 at the front face 18 of the bone anchor 10. On the other side of the bone anchor 10 at the rear face 24, the inner catheter 30 is connected to the rear connector 26. The connections of the outer catheter 28 and the inner catheter 30 to either side of the passage 14 create a continuous fluid-tight connection from the outer catheter 28 to the inner catheter 30. The front connector 16 and the rear connector 26 shown in FIGS. 1-3 are easy connect tube couplings utilizing a press fit connection between the connectors 16 and 26 and the catheter tubes 28 and 30. However, it is contemplated that any number of attachment mechanisms and alternate designs may be used in place of the connectors 16 and 26 to secure devices to or through the bone anchor 10. For instance, in some examples, an external device may screw into the front face 18 or the rear face 24 of the bone anchor 10.

As further shown in FIG. 3, the inner catheter 30 is a larger diameter than the outer catheter 28. This may be helpful to stabilize the segment of the inner catheter 30 located between the bone anchor 10 and the tympanic membrane (TM). As will be recognized by one skilled in the art, the stability of the inner catheter 30 may be particularly important in situations in which the bone anchor 10 is placed for long-term use.

Turning now to FIG. 4, the illustrated example shows the bone anchor 10 from FIGS. 1-3 located within the EAC after the anchor pins 21 have been deployed. The outer catheter 28 and inner catheter 30 have been attached to either side of the bone anchor 10 creating a continuous fluid-tight connection through the body 12 of the bone anchor 10. Also, in the example in FIG. 4, the inner catheter 30 is shown extending from the bone anchor 10, passing through the TM and terminating adjacent to the round window membrane (RWM). As further shown in FIG. 4, the outer catheter 28 is shown extending from the bone anchor 10, through the ear canal and originating from a pump 32. As configured in FIG. 4, the pump 32 may drive fluid through the catheter tubes to deliver the fluid to the RWM and/or cochlea. Accordingly, medication can be delivered to the RWM and/or cochlea. It is contemplated that in other embodiments of the bone anchor 10, the ancillary devices (pumps, catheters, hearing aids, etc.) may be configured for other purposes, such alternate configurations also benefiting from the stability provided by the bone anchor 10 described herein.

It is contemplated that in some embodiments of the bone anchor 10, the outer catheter 28 and inner catheter 30 may be permanently attached to the bone anchor 10. It is further envisioned that in other embodiments just the inner catheter 30 may be permanently attached to the bone anchor 10, while the outer catheter 28 may be detachable. It is also contemplated that both the inner catheter 30 and the outer catheter 28 may both be detachable from the bone anchor 10.

In yet another example, the bone anchor 10 may be incorporated into a hearing aid system for use in instances of conductive hearing loss. The hearing aid system may include a vibrating element secured to the bone anchor 10. The vibrating element may transfer vibrations through a pin into the bony wall of the cochlea. As such, the bone anchor 10 and hearing aid system may be a replacement for the current BAHA implants often used in instances of conductive hearing loss. As further shown, the hearing aid system may further include a receiver working in cooperation with the vibrating element. It is contemplated that in some versions of the hearing aid system, the receiver may be located outside of the ear canal and may communicate with the vibrating element. In other embodiments, the receiver may be located within the EAC. In fact, in certain embodiments, the receiver may also be the vibrating element that transfers vibrations to the bony wall of the cochlea.

While described herein as an outer ear bone anchor 10, it is contemplated that the anchor 10 may be adapted to secure to any portion of the structure of the EAC. For example, the anchor pins 21 may be adapted to be secured within the cartilaginous portion of the EAC. There may be other structure within the EAC that may be used to secure the anchor 10 within the EAC, as will be recognized by one with skill in the art.

It should be noted that various changes and modifications to the presently preferred embodiments described herein will be apparent to those skilled in the art. Such changes and modifications may be made without departing from the spirit and scope of the present invention and without diminishing its attendant advantages.

I claim:

1. An outer ear bone anchor to be stabilized within a person's external auditory canal, the outer ear bone anchor comprising:
   a body; and a plurality of anchor pins, each of the anchor pins including a first end and a second end such that, when the first end of each of the anchor pins is secured to the external auditory canal, the second end of each of the plurality of anchor pins stabilize the body within the external auditory canal, wherein the plurality of anchor pins form a portion of an anchoring mechanism, wherein the anchoring mechanism includes a deployment mechanism adapted to move the anchor pins from a pre-deployed position to a deployed position, wherein the deployment mechanism includes a gear with a first set of teeth adapted to engage one or more of the plurality of anchor pins and a second set of teeth to engage a deployment tool.

2. The outer ear bone anchor of claim 1 wherein the plurality of anchor pins include teeth to engage the first set of teeth of the gear.

3. The outer ear bone anchor of claim 2 wherein each of the plurality of anchor pins mate with one common gear.

4. The outer ear bone anchor of claim 1 wherein the body forms a passage from a front face of the body to a rear face of the body.

5. The outer ear bone anchor of claim 4 wherein the body further includes a front connector located adjacent to an opening of the passage at the front face and a rear connector located adjacent to an opening of the passage at the rear face.

6. The outer ear bone anchor of claim 5 wherein the body further includes an outer catheter secured to the front connector and an inner catheter secured to the rear connector forming a fluid-tight passage from the outer catheter to the inner catheter.

7. An outer ear bone anchor to be stabilized within a person's external auditory canal, the outer ear bone anchor comprising:

a body including a front face, a rear face, and a passage formed through the body extending from the front face to the rear face, the body further including a front face connector located adjacent to an opening of the passage at the front face and a rear face connector located adjacent to an opening of the passage at the rear face; and an anchoring mechanism including a deployment mechanism and a plurality of anchor pins, wherein the deployment mechanism includes a gear with a first set of teeth adapted to engage one or more of the plurality of anchor pins and a second set of teeth to engage a deployment tool, wherein the plurality of anchor pins include teeth to engage the first set of teeth of the gear, further wherein each of the anchor pins includes a first end and a second end such that, when the first end of each of the anchor pins is secured to the external auditory canal, the second end of each of the plurality of anchor pins stabilizes the body within the external auditory canal.

* * * * *